United States Patent [19]

Blaine

[11] 4,379,792

[45] Apr. 12, 1983

[54] ANTI-INFLAMMATORY COMPOSITION

[75] Inventor: Edward H. Blaine, Chalfont, Pa.

[73] Assignee: Merck & Co., Inc., Rahway, N.J.

[21] Appl. No.: 332,434

[22] Filed: Dec. 21, 1981

Related U.S. Application Data

[63] Continuation-in-part of Ser. No. 316,625, Oct. 30, 1980, abandoned.

[51] Int. Cl.³ .................... A61K 31/40; A61K 31/425
[52] U.S. Cl. .................................... 424/270; 424/274; 424/317
[58] Field of Search ............................... 424/270, 274

[56] References Cited

U.S. PATENT DOCUMENTS

| | | | |
|---|---|---|---|
| 3,161,654 | 12/1964 | Shen | 548/500 |
| 3,647,858 | 5/1982 | Hinkley et al. | 560/11 |
| 3,654,349 | 4/1972 | Shen | 562/428 |
| 4,225,609 | 9/1980 | Cragoe, Jr. et al. | 424/270 |

OTHER PUBLICATIONS

Merck Index, 9th Ed. (1976) p. 176.
Chem. Abst. 89–(1978) 140967 H.

*Primary Examiner*—Stanley J. Friedman
*Attorney, Agent, or Firm*—Alice O. Robertson; Daniel T. Szura

[57] ABSTRACT

A pharmaceutical composition containing an interphenylene 9-thia-11-oxo-12-aza prostanoic acid type renal vasodilator and a non-steroidal anti-inflammatory agent and its use are disclosed.

6 Claims, No Drawings

ANTI-INFLAMMATORY COMPOSITION

CROSS REFERENCE TO RELATED APPLICATIONS

This is continuation-in-part of U.S. Application Ser. No. 316,625 filed Oct. 30, 1980, now abandoned.

BACKGROUND OF THE INVENTION

The present invention is concerned with a pharmaceutical composition containing a renal vasodilator and a non-steroidal anti-inflammatory agent.

Non-steroidal anti-inflammatory agents are known (see e.g., U.S. Pat. Nos. 3,161,654, 3,654,349, 3,647,858). A specific example of this class of compounds is the commercial product known as indomethacin.

Recently, a novel class of prostanoic acid type compounds having pharmacological activity have been disclosed (U.S. Pat. No. 4,225,609). These compounds are especially effective renal vasodilators.

It has been discovered that the combination of these renal vasodilator compounds and the non-steroidal anti-inflammatory agents produces a composition having enhanced pharmacological activity.

SUMMARY OF THE INVENTION

A pharmaceutical composition containing an interphenylene-9-thia-11-oxo-12-aza-prostanoic acid type renal vasodilator and a non-steroidal anti-inflammatory agent.

DETAILED DESCRIPTION OF THE INVENTION

An embodiment of the invention is a pharmaceutical composition useful for treating inflammation containing (i) a renal vasodilator compound of the formula

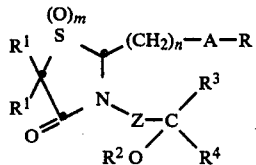
(I)

wherein
R is carboxy, a carboxy salt, a carboxy ester of the formula COOR$^5$ wherein R$^5$ is C$_{1-10}$ alkyl, or CONHR$^6$ wherein R$^6$ is amino or methylsulfonyl;
A is a p-phenylene or a m-phenylene or substituted phenylene derivative in which one or two of the phenylene hydrogens is replaced by a methyl or a halo substituent, or 2,5-thienylene or 2,5-furylene;
n is 3 or 4;
m is 0, 1, or 2;
R$^1$ is hydrogen, deuterium, or methyl;
Z is alkylene or unsaturated alkylene having from 2-3 carbon atoms;
R$^2$ is hydrogen or lower alkanoyl;
R$^3$ is hydrogen or straight chain C$_{1-3}$ alkyl; and
R$^4$ is lower straight chain or branched alkyl having from 3-7 carbon atoms, an unsaturated alkyl having from 3-7 carbon atoms, or a substituted lower alkyl selected from polyfluoro alkyl of from 3-7 carbon atoms and lower alkoxy methylene; or R$^3$ and R$^4$ taken together with the carbon atom connecting R$^3$ or R$^4$ is a cyclic substituent selected from a bridged or unbridged alicyclic ring of from 5-9 carbon atoms or a heterocyclic ring containing sulfur or oxygen and from 5-7 ring-forming carbon atoms;
and (ii) a non-steroidal anti-inflammatory compound.

A preferred (i) compound has the formula

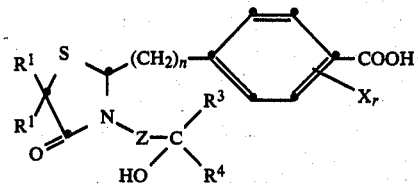

wherein
X is chlorine or methyl;
r is 0, 1, or 2;
n is 3 or 4;
R$^1$ is hydrogen, deuterium, or methyl;
Z is ethylene, trimethylene, cis or transpropenylene, or propynylene;
R$^3$ is hydrogen or lower alkyl of 1-3 carbon atoms; and
R$^4$ is 4-pentenyl, 5,5,5-trifluoropentyl, or lower straight or branched chain alkyl of 3-7 carbon atoms, or

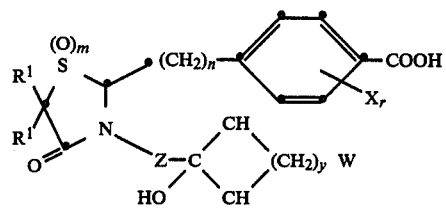

wherein
X is chlorine or methyl;
r is 0, 1, or 2;
n is 3 or 4;
m is 0, 1, or 2;
R$^1$ is hydrogen, deuterium, or methyl;
Z is ethylene, trimethylene, propenylene, or propynylene;
y is 0, 2, or 3; and
W is polymethylene of 2-6 carbon atoms.

A more preferred (i) compound is selected from
4-[3-[3-(3-hydroxyoctyl)-4-oxo-2-thiazolidinyl]-propyl]benzoic acid and
4-[3-[3-[2(1-hydroxycyclohexyl)ethyl]-4-oxo-2-thiazolidinyl]propyl]benzoic acid.

and individual isomers thereof. A still more preferred (i) compound is the (+) enantiomer of 4-[3-[3-[2-(1-Hydroxycyclohexyl)ethyl]-4-oxo-2-thiazolidinyl]-propyl]benzoic acid.

Non-steroidal anti-inflammatory compounds are exemplified by indomethacin, ibuprofen, naproxen, piroxicam and the like. A preferred non-steroidal antiinflammatory compound is indomethacin.

The composition may contain varying amounts of (i) and (ii). The weight ratio of (i):(ii) may range from 1.7:1 to 1:26; preferably from 1:1 to 1:26; more preferably from 1:7 to 1:26; and most preferably from 1:15 to 1:26. In addition to the active ingredients (i) and (ii) the composition may also contain other conventional pharmaceutically acceptable compounding ingredients, as necessary or desired. Such ingredients are generally referred to as carriers or diluents. Conventional procedures for preparing such compositions in appropriate dosage forms may be utilized. Whatever the dosage form, it will contain a therapeutically effective amount of the present composition.

The present compositions may be administered orally or other than orally e.g., parenterally, by insufflation, topically, rectally, etc.; using appropriate dosage forms, e.g., tablets, capsules, suspensions, solutions and the like for oral administration, suspension emulsions and the like for parenteral administration; ointments and the like for topical administration.

Treatment dosage for human beings may be varied as necessary. Generally, daily dosages of the present composition may range from about 550 to about 27 mg; preferably from 400 to about 60 mg; more preferably from about 200 to about 120 mg, using the appropriate dosage form and mode of administration.

The present compositions provide for an improved method of treating inflammation in patients who may have or may develop impaired renal function. It is known that administration of a non-steroidal, anti-inflammatory agent such as indomethacin may result in reducing renal function of a human patient. Where the patient already has renal function impaired, of course, the non-steroidal anti-inflammatory might cause further impairment-and, thus, this patient would be denied the benefit of the inflammation relief offered by the non-steroidal inflammatory.

In vivo testing in test animals (dogs) has demonstrated that the present compositions prevent (or restore) impairment of renal function. Specifically, indomethacin alone when administered intravenously to test animals decreased effective renal plasma flow (ERPF) by about 37% and glomelular filtration rate (GFR) by about 28%, two criteria of renal function. When 4-[3-[3-([2-(1-hydroxycyclohexyl)ethyl]-4-oxo-2-thiazolidinyl]-propyl]benzoic acid, was administered to the test animals after the indomethacin, GFR was restored to normal within about two hours and the ERPF rose to almost twice the preindomethacin treatment level. The restoration of the GFR is especially surprising and coupled with the increase in ERPF indicates that the present compositions can be used in patients, requiring anti-inflammatory therapy without impairing renal function.

The formula I compounds are fully disclosed in U.S. Pat. No. 4,225,609 and to the extent necessary that disclosure is incorporated herein by reference.

A proces for preparing the individual enantiomers of the formula I compounds is illustrated by the following examples. The underlined numbers in Example 1 identify the products as shown in the Flow Sheet.

EXAMPLE 1

Resolution of Racemic 4-{3-[3-[2-(1-hydroxycyclohexyl)-ethyl]-4-oxo-2-thiazolidinyl]propyl}benzoic Acid

FLOW SHEET

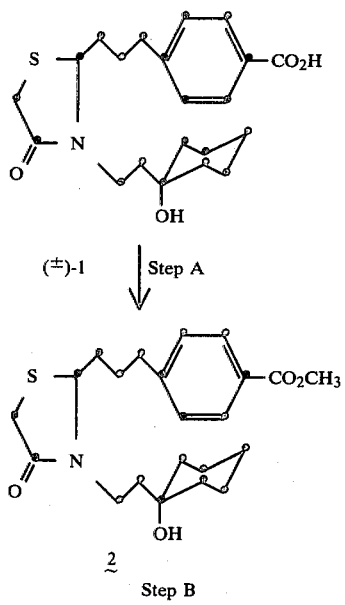

Step A

2

Step B

FLOW SHEET

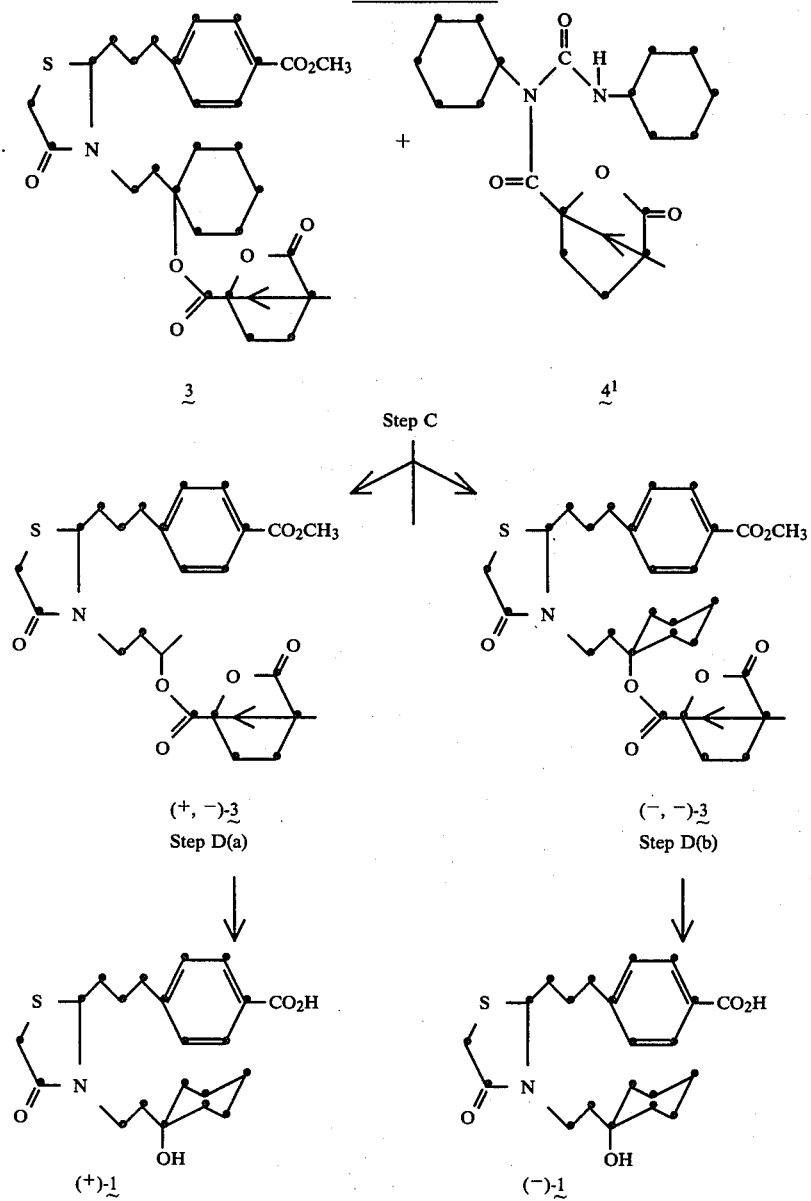

[1] This byproduct acylurea 4 is separable by chromatography.

Step A. Preparation of (±)-Methyl 4-[3-[3-[2-(1-Hydroxycyclohexyl)ethyl]-4-oxo-2-thiazolidinyl]propyl]benzoate (2)

To a freshly-prepared solution of (±)-4-[3-[3-[2-(1-hydroxycyclohexyl)ethyl]-4-oxo-2-thiazolidinyl]-propyl]benzoic acid (1) (10 g, 25.6 mmol) in dry N,N-dimethylformamide (86 ml) contained in a 250 ml round bottom flask is added finely-ground potassium carbonate (3.54 g, 25.6 mmol) followed by methyl iodide (1.6 ml, 25.6 mmol). The resulting suspension is protected from atmospheric moisture with a magnesium sulfate drying tube and is stirred at room temperature for 19.5 hours. The reaction mixture is poured into water (175 ml) contained in a separatory funnel and then is extracted with ether (3×40 ml). The organic extracts are combined, washed with saturated aqueous sodium bicarbonate (3×30 ml), dried over sodium sulfate and filtered. Evaporation (*in vacuo*) of the filtrate leaves the desired ester 2 as a pale yellow oil (10.55 g): tlc, $R_f=0.4$ (homogeneous, UV detection) on silica gel with ethyl acetate:hexane (7:3; v:v) as eluent; ir (2% solution in chloroform) 3400 (w), 1710 (s), 1600 (s) and 1280 (s) $cm^{-1}$.

Step B. Preparation of Methyl 4-[3-[3-[2-(1-(−)-camphanyloxy)cyclohexyl)-ethyl]-4-oxo-2-thiazolidinyl]propyl]benzoate (3)

To a solution of (±)-methyl 4-[3-[3-[2-(1-hydroxycyclohexyl)ethyl]-4-oxo-2-thiazolidinyl]propyl]-benzoate (2) (38.37 g, 94.6 mmol) in methylene chloride (189 ml) are added (−)-camphanic acid (20.64 g, 104.1 mmol) and 4-dimethylaminopyridine (5.77 g, 47.3 mmol). The resulting solution is cooled to 0° C. and treated with a solution of N,N'-dicyclohexylcarbodiimide (23.38 g, 113.52 mmol) in methylene chloride (180 ml) added slowly with stirring over 15 minutes. Thereby is obtained a heterogeneous mixture which is stirred at ambient temperature for 22 hours. The reaction mixture is filtered to remove the insoluble solid (N,N'-dicyclohexylurea). The filtrate is washed with 0.2 N-hydrochloric acid (2×60 ml) and water (2×80 ml), dried over sodium sulfate and filtered. Evaporation (in vacuo) of the filtrate affords a brown, oily residue (semi-solid): tlc on silica gel with chloroform:methanol (98:2; v:v) indicates that the product 3, $R_f=0.3$, is accompanied by starting material 2 (ca. 5%) and traces of 4-dimethylaminopyridine.

The oily residue is "flash chromatographed" on silica gel (600 g, 230–400 mesh, E. Merck) using chloroform-methanol (98:2; v:v) as eluent and a flow rate sufficient to move the solvent front at 1" per minute. Thereby is eluted product 3 (ca. 55 g as a yellow solid) which is contaminated with N-((−)-camphanyl)-N,N'-dicyclohexylurea (4). Product 3 is used as such in Step C described below.

Step C. Separation of Mixture 3 Into Diastereomeric Components (−,−)-3 and (+,−)-3

(a) Isolation of (−,−)3-Yellow solid 3 (ca. 55 g from Step B above) is triturated with ethyl acetate hexane (1:1; v:v; 300 ml) at room temperature for 1 hour to provide a heterogeneous mixture which is filtered. The collected, pale yellow solid (ca. 25 g of impure (−,−)−3) is recrystallized six times from ethyl acetate to afford pure diastereomer[1] (−,−)-3 as colorless crystals (8.85 g), mp 163°–164° C.; $[\alpha]_D^{22}=-47.3°$ (c 0.58, CHCl$_3$).

[1]Pmr analysis of (−,−)-3 and (+,−)-3 using the Europium shift reagent Eu(fOd)$_3$ shows that each of these materials is a single diastereomer.

(b) Isolation of (+,−)-3—The trituration filtrate from Step C (a) above is evaporated in vacuo to provide a residue[2] (ca. 24 g) consisting essentially of (+,−)-3 and byproduct 4. This residue is "flash chromatographed" in two separate 12 g portions as described below. A 12 g portion is applied in chloroform to a silica gel column (ca. 350 g, 230–400 mesh, E Merck, 60 mm in diameter×10" in length) which is eluted first with 30% ethyl acetate in hexane (2.4 L) at a flow rate sufficient to move the solvents from 1" per minute to remove the byproduct 4. Continued elution at the same flow rate with 40% ethyl acetate in hexane (1 L), 50% ethyl acetate in hexane (2 L) and 60% ethyl acetate in hexane (1 L) provides (+,−)-3. From the two "flash chromatographies" is obtained a pale yellow solid (15 g), $[\alpha]_D^{22}=+26.5°$ (c 0.57, CHCl$_3$). This solid is recrystallized from ethyl acetate to constant rotation. Thereby is obtained pure diastereomer (+,−)−3[3] as colorless crystals (10.55), mp 130°–132° C.; $[\alpha]_D^{22}=+37.2°$ (c 0.61, CHCl$_3$).

[2]This residue can be analyzed by tlc: $R_f=0.12$ for (+,−)-3 and $R_f=0.36$ for 4 on silica gel with ethyl acetate: hexane (3:7; v:v) elution followed by detection (dipping tlc plate in 5% sulfuric acid in ethanol and subsequent heating on a hot plate).
[3]See footnote (1) on page 11.
[4]Azeotropic distillation ensures the removal of traces of moisture.
[5]The pH of this aqueous mixture should be checked with Congo red test paper; if not sufficiently acidic, additional 0.1 N hydrochloric acid should be added prior to separation of the layers.

Step D. Hydrolysis of (+,−)-3 and (−,−)-3

(a) Preparation of (+)-4-3-[3-[2-(1-Hydroxycyclohexyl)ethyl]-4-oxo-2-thiazolidinyl]-propyl benzoic Acid To toluene (102 ml) contained in a 250 ml round bottom flask is added crushed solid potassium hydroxide (3.83 g, 68.3 mmol). The resulting heterogeneous mixture is heated at reflux until ca. 20 ml of distillate is collected[4] and then is cooled to room temperature. To the cooled heterogeneous mixture is added (+,−)-3 (4 g, 6.83 mmol) followed by dicyclohexyl-18-Crown-6 (12.72 g, 34.2 mmol). The resulting reaction mixture is protected from atmospheric moisture with a magnesium sulfate drying tube and is vigorously stirred and heated at 40° C. (oil bath) for 1 hour. Then the drying tube is removed, water (80 ml) is added to the brown reaction mixture and stirring and heating at 40° C. are continued for 45 hours. After cooling to room temperature, the reaction mixture is poured slowly into cold, excess N hydrochloric acid (200 ml) with vigorous stirring. The acidic,[5] aqueous mixture is transferred to a separatory funnel and the layers are allowed to separate. The aqueous layer (acidic phase) is extracted with chloroform (4×100 ml). The toluene and chloroform layers are combined, washed with water (2×100 ml), dried over sodium sulfate and filtered. Evaporation (in vacuo) of the filtrate leaves an oily residue which is triturated with ether at room temperature to afford an insoluble, colorless solid. The solid is collected, washed with ether and dried to give 2.04 g (76%) of (+)-1: tlc, $R_f=0.26$ (homogeneous, UV detection) with chloroform:methanol (9:1; v:v) on silica gel; identical by tlc to 1. Recrystallization from methanol affords pure enantiomer (+)-1 as colorless crystals (1.1 g), mp 139.5–140.5° C.; $[\alpha]_D^{22}+70.0°$ (c 0.47, CHCl$_3$); ir (KBr pellet) 3270, 1690, 1640 and 1260 cm$^1$; pmr (CDCl$_3$) 8.05 (2H, d), 7.28 (2H, d), 6.49 (2H, bs, OH and CO$_2$H), 4.75 (H, bm), 3.56 (2H,s), 2.68 (2H, t) and 1.60 (bc envelope).

Anal. Calcd. for C$_{21}$H$_{29}$NO$_4$S: C, 64.42; H, 7.47; N, 3.58 Found: C, 64.57; H, 7.81; N, 3.51

(b) Preparation of (−)-4-[3-[3-[2-(1-hydroxycyclohexyl)ethyl]-4-oxo-2-thiazolidinyl]propyl]benzoic Acid The hydrolysis of the pure diastereomer (−,−)-3 is carried out exactly as described above for (+,−)-3 in Step D (a). Thereby is obtained pure enantiomer (−)-1 as colorless crystals (1.24 g), mp 140°–141° C. (from CH$_3$OH); $[\alpha]_D^{22}-68.7°$ (C 0.47, CHCl$_3$); tlc, ir and pmr data identical with those recorded for (+)-1.

Anal. Calcd. for C$_{21}$H$_{29}$NO$_4$S: C, 64.42; H, 7.47; N, 3.58 Found: C, 64.48; H, 7.72; N, 3.72

EXAMPLE 2

(A) Preparation of Methyl 4-[3-[3-hydroxyoctyl)-4-oxo-2-thiazolidinyl]propyl]-benzoatebenzoic A solution of racemic 4-[3-[3-(3-hydroxyoctyl)-4-oxo-2-thiazolidinyl]propyl]benzoic acid (13.13 g; 0.03336 mole) in dimethylformamide (66 ml) is treated with potassium carbonate (9.22 g; 0.06672 mole) and methyliodide (5.68 g; 0.04003 mole) and the resulting mixture is stirred at room temperature for 22 hours.

The reaction mixture is poured into cold water (330 ml). The oily layer is extracted with ether. The combined extracts are washed well with water and dried over magnesium sulfate. The solvent is removed under vacuum to give the methyl 4-[3-[3-(3-hydroxyoctyl)-4-oxo-2-thiazolidinyl]propyl]benzoate racemate as an orange oil, yield 13.60 g.

(B) Separation of the Two Racemic Modifications of Methyl 4-[3-[3-(3-hydroxyoctyl)-4-oxo-2-thiazolidinyl]propyl]-benzoate The two racemic modifications that comprise methyl 4-[3-[3-(3-hydroxyoctyl-4-oxo-2-thiazolidinyl]propyl]-benzoate as obtained above in A are separated by liquid chromatography using a Prep LC/System 500 liquid chromatograph manufactured by Waters Associate, Inc. The chromatographic column in this instrument is a Prep PAK-500/$C_{18}$ silica cartridge with dimensions 5.7×30 cm. The solvent mixture used is hexane-isopropyl alcohol, 95:5 (v/v). Thirteen g of the mixed racemates of the methyl ester after elution with 60 L of the solvent system gives 4.8 g of a front running fraction designated *Racemate B-methyl ester* and 6.9 g of a slower running fraction designated *Racemate A-methyl ester*. The two fractions can also be differentiated by thin layer chromatography on silica with 2% methanol in chloroform (v/v) as the mobile phase. In this system, Racemate B-methyl ester has $R_f$ 0.32, and Racemate A-methyl ester has $R_f$ 0.28.

(C-1) Preparation of Diastereomeric Camphanates from Racemate A of Methyl 4-[3-[3-(3-hydroxyoctyl)-4-oxo-2-thiazolidinyl]propyl]-benzoate N,N'-Dicyclohexylcarbodiimide (6.2 g, 30 mmole) in $CH_2Cl_2$ is added to a solution at 0° C. of Racemate A of methyl 4[3-[3-(3-hydroxyoctyl)-4-oxo-2-thiazolidinyl]-propyl]benzoate (10.0 g, 24.6 mmole), (1S)-(−)- -camphanic acid (5.39 g, 27.2 mmole) and 4-dimethylaminopyridine (1.5 g, 12.3 mmole) in $CH_2Cl_2$ (25 ml). The mixture is stirred at 27° C. for 6 hours. Precipitated dicyclohexylurea is removed by filtration. The filtrate is washed with 0.1 N hydrochloric acid and dried. Removal of solvent gave the crude mixed diastereomeric camphanates of Racemate A-methyl ester.

(C-2) Preparation of Diastereomeric Camphanates from Racemate B of Methyl 4-[3-[3-(3-hydroxyoctyl)-4-oxo-2-thiazolidinyl]propyl]-benzoate By following the procedure described in Step C-1 but substituting Racemate B-methyl ester for the Racemate A-methyl ester there is obtained the crude mixed diastereomeric camphanates of Racemate B-methyl ester.

(D-1) Isolation of the Levorotatory Diasteromeric Camphanate of Racemate A of Methyl 4-[3-[3-(3-hydroxyoctyl)-4-oxo-2-thiazolidinyl]propyl]-benzoate The crude mixed diastereomeric camphanates or Racemate A-methyl ester (Step C-1) are triturated with 1:1 ethyl acetate-hexane (100 ml of solvent mixture per 15 g of esters). The insoluble material is collected on a filter. The filtrate containing the bulk of the dextrorotatory diastereomer is set aside. The solid is recrystallized three times from ethyl acetate to give the levorotatory diastereomeric camphanate of Racemate A-methyl ester (chemical name: (−)-diastereomer of racemate A methyl 4-[3-[3-(1S)- -camphanyloxy)octyl]-4-oxo-2-thiazolidinyl]propyl]benzoate).

(D-2) Isolation of the Dextrorotatory Diastereomeric Camphanate of Racemate A of Methyl 4-[3-[3-(3-hydroxyoctyl)-4-oxo-2-thiazolidinyl]propyl]-benzoate Evaporation of solvents from the filtrate obtained by trituration of mixed diastereomeric camphanate of racemate A-methyl ester gives an oil which crystallizes on standing. This solid is recrystallized three times from ethyl acetate to yield the dextrorotatory diastereomeric camphanate of racemate A-methyl ester. (Chemical name: (+)-diastereomer of racemate A methyl 4-[3-[3-(3-((1S)- -camphanyloxy-octyl)-4-oxo-2-thiazolidinyl]propyl]benzoate). (D-3) Isolation of the Levorotatory Diastereomeric Camphanate of Racemate B of Methyl 4-[3-[3-(3-hydroxyoctyl)-4-oxo-2-thiazolidinyl]propyl]benzoate Treatment of the crude mixed diastereomeric camphanates of Racemate B-methyl ester (Step C-2) exactly as in D-1 yields the levorotatory diastereomeric camphanate of Racemate B-methyl ester (chemical name: (−)-diastereomer or racemate B-methyl 4-[3-[3-(3-((1S)- -camphanyl-oxy)octyl-4-oxo-2-thiazolidinyl]propyl benzoate).

(D-4) Isolation of the Dextrorotatory Diastereomeric Camphanate of Racemate B of Methyl 4-[3-[3-(3-hydroxyoctyl)-4-oxo-2-thiazolidinyl]propyl]-benzoate Treatment of the filtrate from the isolation of the camphanate of D-3 exactly as described in Step D-2 yields the dextrorotatory diastereomeric camphanate of Racemate B-methyl ester (chemical name: (+)-diastereomer or racemate B-methyl 4-[3-[3-(3-((1S)- -camphanyloxy)octyl)-4-oxo-2-thiazolidinyl]propyl]benzoate.

(E-1) Preparation of the (−)-Enantiomer of Racemate A of 4-[3-[3-(3-hydroxyoctyl-4-oxo-2-thiazolidinyl]propyl]-benzoic acid Potassium hydroxide (finely crushed pellets) (3.83 g,, 68.3 mmoles) is added to toluene (100 ml). The mixture is stirred and treated with the levorotatory diastereomeric camphanate of Racemate A-methyl ester (D-1) (4 g, 6.82 mmoles) and dicyclohexyl-18-crown-6 (12.7 g, 34.2 mmole). The mixture is then stirred and heated at 40° C. for 1 hour. Water (80 ml) is added to the reaction mixture and stirring at 40° C. is continued for 45 hours. The mixture is then poured into 1 N hydrochloric acid (200 ml). The toluene layer is separated, washed with water and dried. The solvent is evaporated at reduced pressure. The residual oil is triturated with acetonitrile to give the waxy solid (−)-enantiomer of racemate A of 4-[3-[3-(3-hydroxyoctyl)-4-oxo-2-thiazolidinyl]propyl]-benzoic acid.

(E-2) Preparation of the (+)-Enantiomer of Racemate A of 4-[3-[3-(3-hydroxyoctyl)-4-oxo-2-thiazol-idinyl]propyl benzoic acid Hydrolysis of the dextrorotatory diastereomeric camphanate of Racemate A-methyl ester (Step D-2) exactly as described in Step E-1 yields the waxy solid (+)-enantiomer of Racemate A of 4-[3-[3-(3-hydroxyoctyl-4-oxo-2-thiazolidinyl]propyl]benzoic acid.

(E-3) Preparation of the (−)-Enantiomer of Racemate B of 4-[3-[3-(3-hydroxyoctyl)-4-oxo-2-thiazolidinyl]propyl]-benzoic acid Hydrolysis of the levorotatory diastereomeric camphanate of Racemate B-methyl ester (Step D-3) exactly as described in Step E-1 yields the waxy solid (−)-enantiomer of Racemate B of 4-[3-[3-(3-hydroxyoctyl-4-oxo-2-thiazolidinyl]propyl]benzoic acid.

(E-4) Preparation of the (+)-Enantiomer of Racemate B of 4-[3-[3-(3-hydroxyoctyl)-4-oxo-2-thiazolidinyl]propyl]-benzoic acid Hydrolysis of the dextrorotatory diastereomeric camphanate of Racemate B-methyl ester (Step D-4) exactly as described in Step E-1 yields the waxy solid (+)-enantiomer of Racemate B of 4-[3-[3-(3-hydroxyoctyl)-4-oxo-2-thiazolidinyl]propyl]benzoid acid.

Claims to the invention follow.

I claim:

1. A pharmaceutical composition useful for treating inflammation containing (i) a renal vasodilator compound of the formula

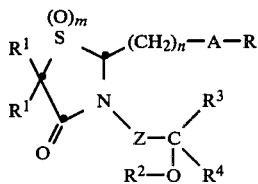

wherein
- R is carboxy, a carboxy salt, a carboxy ester of the formula $COOR^5$ wherein $R^5$ is $C_{1-10}$ alkyl, or $CONHR^6$ wherein $R^6$ is amino or methylsulfonyl;
- A is a p-phenylene or a m-phenylene or substituted phenylene derivative in which one or two of the phenylene hydrogens is replaced by a methyl or a halo substituent;
- n is 3 or 4;
- m is 0, 1, or 2;
- $R^1$ is hydrogen, deuterium, or methyl;
- Z is alkylene or unsaturated alkylene having from 2–3 carbon atoms;
- $R^2$ is hydrogen or lower alkanoyl;
- $R^3$ is hydrogen or straight chain $C_{1-3}$ alkyl; and
- $R^4$ is lower straight chain or branched alkyl having from 3–7 carbon atoms, an unsaturated alkyl having from 3–7 carbon atoms, or a substituted lower alkyl selected from polyfluoro alkyl of from 3–7 carbon atoms and lower alkoxy methylene; or
- $R^3$ and $R^4$ taken together with the carbon atom connecting $R^3$ and $R^4$ is a cyclic substituent selected from a bridged or unbridged alicyclic ring of from 5–9 carbon atoms or a heterocyclic ring containing sulfur or oxygen and from 5–7 ring-forming carbon atoms. and (ii) inclomethacin wherein the weight ratio i:ii ranges from 1.7:1 to 1:26.

2. The composition of claim 1 wherein said (i) compound has the formula

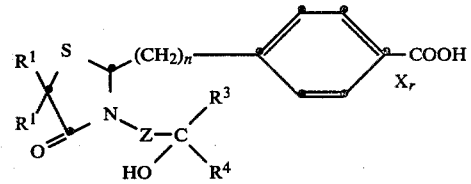

wherein
- X is chlorine or methyl
- r is 0, 1, or 2;
- n is 3 or 4;
- $R^1$ is hydrogen, deuterium, or methyl;
- Z is ethylene, trimethylene, cis or trans-propylene, or propynylene;
- $R^3$ is hydrogen or lower alkyl of 1–3 carbon atoms; and
- $R^4$ is 4-pentenyl, 5,5,5-trifluoropentyl, or lower straight or branched chain alkyl of 3–7 carbon atoms or

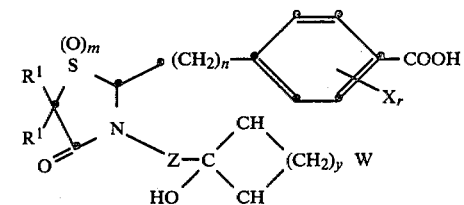

wherein
- X is chlorine or methyl
- r is 0, 1, or 2;
- n is 3 or 4;
- m is 0, 1, or 2;
- $R^1$ is hydrogen, deuterium, or methyl
- Z is ethylene, trimethylene, propenylene, or propynylene;
- y is 0, 2, or 3; and
- W is polymethylene of 2–6 carbon atoms.

3. The composition of claim 2 wherein said (i) compound is 4-[3-[3-(3-hydroxyoctyl)-4-oxo-2-thiazolidinyl]propyl]benzoic acid.

4. The composition of claim 2 wherein said (i) compound is 4-[3-[3-(2-(1-hydroxycyclohexyl)-ethyl]-4-oxo-2-thiazolidinyl]propyl]benzoic acid.

5. The composition of claim 4 wherein said (i) compound is the (+) enantiomer.

6. A method of treating inflammation in a human which comprises administering to said human a composition of claim 1.

* * * * *